(12) United States Patent
Reihl et al.

(10) Patent No.: US 7,824,382 B2
(45) Date of Patent: Nov. 2, 2010

(54) NEEDLE TIP

(75) Inventors: Bruno Reihl, Wilen be Wollerau (CH); Hanspeter Heiniger, Lotzwil (CH)

(73) Assignee: Roche Diagnostics International AG, Steinhausen (CH)

( * ) Notice: Subject to any disclaimer, the term of this patent is extended or adjusted under 35 U.S.C. 154(b) by 1287 days.

(21) Appl. No.: 11/287,581

(22) Filed: Nov. 23, 2005

(65) Prior Publication Data

US 2006/0135917 A1   Jun. 22, 2006

Related U.S. Application Data

(63) Continuation of application No. 11/098,012, filed on Apr. 1, 2005, now abandoned, which is a continuation of application No. PCT/EP2003/010891, filed on Oct. 1, 2003.

(51) Int. Cl.
*A61M 5/00* (2006.01)
*A61B 17/04* (2006.01)
*A61B 17/06* (2006.01)

(52) U.S. Cl. .................. 604/272; 604/264; 606/144; 606/223

(58) Field of Classification Search ................ 606/223; 604/272, 164.06
See application file for complete search history.

(56) References Cited

U.S. PATENT DOCUMENTS

| | | | | |
|---|---|---|---|---|
| 3,636,955 A | * | 1/1972 | Kurtz | 606/223 |
| 4,513,747 A | * | 4/1985 | Smith | 606/223 |
| 5,064,411 A | * | 11/1991 | Gordon, III | 604/48 |
| 5,178,628 A | * | 1/1993 | Otsuka et al. | 606/223 |
| 5,254,106 A | * | 10/1993 | Feaster | 604/272 |
| 5,476,480 A | * | 12/1995 | Matsutani et al. | 606/222 |
| 5,478,327 A | * | 12/1995 | McGregor et al. | 604/272 |
| 5,591,139 A | * | 1/1997 | Lin et al. | 604/264 |
| 5,676,675 A | * | 10/1997 | Grice | 606/144 |
| 5,683,416 A | * | 11/1997 | McGregor et al. | 606/223 |
| 2004/0098048 A1 | * | 5/2004 | Cunningham et al. | 606/223 |
| 2004/0106948 A1 | * | 6/2004 | Cunningham | 606/223 |

FOREIGN PATENT DOCUMENTS

| | | |
|---|---|---|
| DE | 3230150 | 3/1983 |
| DE | 0481566 A1 | 4/1992 |
| DE | 4416976 | 11/1995 |
| DE | 4446677 | 7/1996 |
| DE | 19614780 | 10/1997 |
| DE | 29901139 U1 | 4/1999 |
| DE | 19911970 | 9/2000 |
| EP | 1036571 | 9/2000 |
| GB | 717594 | 10/1954 |

* cited by examiner

*Primary Examiner*—Nicholas D Lucchesi
*Assistant Examiner*—Ian K Holloway
(74) *Attorney, Agent, or Firm*—Dorsey & Whitney LLP

(57) ABSTRACT

A needle for medical uses, for example for inserting a dialysis membrane into human or animal tissue, wherein the needle has an end portion made of solid material and provided with at least two areas which intersect a longitudinal axis of the needle and each other whereby at least one line or point of intersection is formed between the at least two areas, the line or point of intersection in a needle region adjacent to the end portion.

19 Claims, 3 Drawing Sheets

NEEDLE TIP

CROSS-REFERENCE TO RELATED APPLICATION(S)

This application is a continuation of U.S. patent application Ser. No. 11/098,012, filed on Apr. 1, 2005, which is a continuation of International Patent Application No. PCT/EP2003/010891, filed on Oct. 1, 2003, which claims priority to German Application No. 102 47 022.7, filed on Oct. 9, 2002, the contents of which are incorporated in their entirety by reference herein.

BACKGROUND

The present invention relates to needles for medical applications, for example for insertion into tissue. More particularly, it relates to a needle for insertion of a dialysis membrane into human or animal tissue, for example, a needle with an elongate needle region and an end portion which adjoins the needle region and forms a needle tip for insertion into tissue, wherein the needle carries or has an associated dialysis membrane.

It may be necessary, for a wide variety of reasons, to introduce a medical device or a test device into a tissue, for example a human, animal or other biological tissue. To do this, the surface of the tissue must be penetrated, and, in doing so, the opening made in the tissue, and the force applied to penetrate the surface, should be as small as possible in order to minimize any pain or tissue lesions caused. At the same time, however, the requirements of the medical treatment, application, procedure or test must be able to be satisfied, for which reason large insertion openings and depths of insertion are often needed. To introduce or remove a product, for example a medical, pharmaceutical or cosmetic fluid, or to permit an exchange of a test fluid with the tissue, as is necessary, for example, in dialysis, round hollow needles are used. These hollow needles are beveled at their distal or tissue penetrating end in such a way that an oval ring surface is obtained with a cutting edge forming the tip of the needle. A needle of this kind has been disclosed, in the form of a hypodermic needle, by Therumo Medical Corporation. This needle is additionally beveled in a hyperbola area of the oval surface of the needle tip, so that two bevels are produced which form a sharp tip at the reverse point of the hyperbola.

In microdialysis probes, probe needles are used for conveying a perfusion solution through the tissue, this solution interacting with the tissue environment via a dialysis membrane. Since both a supply line and a discharge line are needed for the perfusion solution, the needles for this reason cannot be made very thin. Instead they generally have a thickness which makes insertion of the needle unpleasant for the user.

The penetration of a needle into a tissue takes place in two stages. First, the surface of the tissue must be penetrated by the tip of the needle. A pressure force which has to be applied in order to do this, and which is referred to hereinafter as the initial penetration force, is lessened by using a fine pointed tip rather than a cutting edge. After the tip of the needle has penetrated into the tissue, the needle region which adjoins the end portion forming the tip penetrates into the tissue. Since this needle region has a thicker cross section, i.e., it is thicker than the end portion of the needle tip, a greater force has to be applied, referred to hereinafter as the complete penetration force, than is necessary for the initial penetration force of the tip. This complete penetration force is lessened by using a cutting edge in contrast to a pointed tip at the needle tip. When configuring the tip area of the needle, a compromise must therefore be found between a fine pointed tip and a cutting edge.

In conventional needles for medical purposes, this requirement has received little attention because needle tips allow little leeway when it comes to their design. For example, tubular needles with a tube or even two tubes for a supply line and a discharge line can be designed in different tip shapes only with difficulty. Burrs often form at the edges, these burrs increasing the force that has to be applied and thus making the penetration of the needle particularly unpleasant for the user. Moreover, in conventional needles, the tip or edge areas of the needle tip often bend when the needle tip is inserted, as a result of which the force to be applied for penetration is further heightened. In particular, needles of microdialysis probes often cannot be made especially pointed or sharp since, in many cases, the dialysis membrane is arranged in or around the needle tip area and could be damaged by sharp edges or points.

SUMMARY

It is therefore an object of the present invention to provide a needle for medical applications, in particular a microdialysis needle, which makes insertion and subsequent, further introduction of the needle easier, lessens the force that has to be applied for penetration, reduces discomfort experienced by the user, and minimizes any changes in the tissue and the needle during insertion of the needle.

In one embodiment, the present invention comprises a needle for medical uses, for example, for inserting a dialysis membrane into human or animal tissue, wherein the needle has an end portion with at least two areas which intersect a longitudinal axis of the needle and each other whereby at least one line or point of intersection is formed between the at least two areas, the line or point of intersection being adjacent to the end portion.

In one embodiment, the present invention comprises a needle for medical uses comprising a needle region and an end portion with at least two areas which intersect a longitudinal axis of the needle and each other whereby one of at least one line or point of intersection is formed between the at least two areas, the at least one line or point of intersection being in the needle region and adjacent to the end portion.

In one embodiment, the present invention comprises a needle for medical applications, which is used for pricking and/or penetrating a tissue, particularly for inserting a dialysis membrane into a human tissue or animal tissue. The needle comprises a end portion (which also might be referred to the distal end portion) that is made of solid material and is provided with at least two areas which intersect a longitudinal axis of the needle and each other in such a way that at least one line and/or one point of intersection is/are formed between the at least two areas. The line or point of intersection is preferably arranged within the circumference of a cross section located inside a needle region of the needle, which is adjacent to the end portion.

The needle according to the present invention is provided for insertion into tissue and has an elongate needle region and an end portion which adjoins the needle region and forms a needle tip. The needle according to the present invention is to be used in particular for insertion of a dialysis membrane into body tissue. The end portion of the needle is made of solid material, i.e., the end portion preferably has no passages, openings, recesses, depressions or the like, and is preferably made of substantially homogeneous material. It is conceivable, however, to provide thin passages or depressions in the end portion as long as these are negligible in relation to the volume of the end portion. The material used can be, for example, a metal or a plastic, for example silicone. The entire needle is preferably made of a single material. It is conceivable, however, for the needle tip to be made of a separate material, or for the end portion to be covered or coated with a suitable material.

According to the presention invention, the end portion has at least two surfaces which, on the one hand, intersect a longitudinal axis of the needle and, on the other hand, intersect each other, as a result of which at least one line of intersection or point of intersection or both may be formed between the at least two surfaces on a top of the end portion. The line of intersection and point of intersection form the tip of the needle and, upon penetration into a tissue, are first to come into contact with the tissue surface. At least one of the lines of intersection preferably forms a cutting edge on the end portion. For this purpose, it is necessary for the two surfaces forming the line of intersection to intersect at an acute angle, in one preferred embodiment, at an angle of less than 20°. In one preferred embodiment, the at least two surfaces of the end portion are configured, and arranged with respect to one another, in such a way that the lines of intersection of the surfaces, i.e., the cutting edges of the end portion of the needle, extend toward a common point of intersection which forms the frontmost point of the needle and, consequently, the needle tip.

It is advantageous if the at least one line of intersection and/or point of intersection lies within the circumference of the needle region. It is also advantageous if a line of intersection, or a cutting edge, and/or the point of intersection lies on a plane of symmetry, preferably on a center line of symmetry, i.e., on the longitudinal axis of the needle, of the cross section of the needle region. In other words, the cutting edges and the point of intersection, which forms the insertion tip of the needle, should be arranged as centrally as possible in the cross section of the needle. However, there are also other possibilities of arranging the at least two surfaces on the end portion within the context of the invention, as an illustrative embodiment set out below will show. The cross section of the needle in the needle region before the end portion can be round, oval or polygonal. For its use as a microdialysis needle, in some preferred embodiments, the needle is configured with a polygonal cross section in its needle region, for example, a rectangular cross section. For its part, the outer circumference of the needle region is formed by several contiguous circumferential surfaces, in some preferred embodiments, four circumferential surfaces, which extend along the longitudinal axis of the needle and which, at the end portion, merge into the surfaces of this end portion, forming an acute angle with these surfaces.

By means of the configurations of the end portion according to the present invention, a pointed tip can be formed on the needle tip so as to lessen the initial penetration force needed for piercing the surface of a tissue, or a cutting edge can be produced in the area of the tip of the needle so as to lessen the complete penetration force needed for complete insertion of the needle into a tissue. In a needle tip according to the present invention, the initial penetration force can preferably be lessened by the pointed tip according to the invention and, at the same time, the complete penetration force can be lessened by the cutting edge according to the invention. Overall, considerably less pressure force therefore has to be applied for inserting the needle into the tissue, as a result of which, for example, a patient experiences less pain or the tissue is less affected and altered.

In accordance with the present invention, the surfaces of the end portion of a needle can be planar or curved or arched. Likewise, they can be partially planar and partially curved. Correspondingly, the lines of intersection of such surfaces are straight or curved. Moreover, at least two surfaces are arranged with mirror symmetry in relation to a plane of symmetry extending along the longitudinal axis of the needle. It is also conceivable for the end portion of the needle to be arranged with mirror symmetry in relation to two mutually perpendicular planes of symmetry which intersect in the longitudinal axis of the needle.

In a preferred embodiment of the invention, two surfaces of the end portion are each configured as cone-shaped partial surfaces which taper toward one another. In this case, the geometric cone vertices belonging to the cone surfaces are offset from one another so that the cone surfaces intersect at an acute angle. In this way, a pointed tip is formed on the longitudinal axis of the needle and, on two opposite sides of the pointed tip, two cutting edges extend in an arc shape to the tip.

In a further embodiment of the present invention, the surfaces of the end portion can be arranged in a pyramid configuration relative to one another, preferably in the form of a four-sided pyramid. In this case, the end portion forms four planar surfaces which intersect in a single point of intersection lying on the longitudinal axis of the needle, so that this point of intersection forms a pointed tip. Advantageously, one surface forms an acute angle with the surface adjoining it on one side, and forms an obtuse angle with the surface adjoining it on the other side. Along the line of intersection of the acute angle, a cutting edge is thus obtained at the end portion of the injection tip. In another embodiment, four surfaces of the end portion do not meet at a single point of intersection, with the result that it is not a pointed tip, but instead a cutting edge that is obtained as the frontmost point of the needle. In this case, two first surfaces which lie opposite one another and extend parallel in one dimension form an angle whose vertex lies on the longitudinal axis of the needle. The two other surfaces which lie opposite one another and likewise extend parallel in one dimension are arranged between the first surfaces and form an angle whose vertex lies on the longitudinal axis nearer to the end portion than the vertex of the first two surfaces. An end portion configured in this manner forms a kind of half pyramid.

In another preferred embodiment of the needle according to the present invention, a needle region with a rectangular cross section, i.e., with a width of cross section longer than its height, is used, and the end portion has two surfaces arranged like facets. For this purpose, two opposite side surfaces of the end portion are arranged obliquely with respect to one another in such a way that they meet in an acute angle on a plane of symmetry of the rectangular cross section. The acute angle can be 20°, for example. The side surfaces can, for example, form the continuation of the lateral circumferential surfaces of the needle region which correspond to the height of the cross section. The two other lateral circumferential surfaces of the needle region, which extend perpendicular to the previous circumferential surfaces, are beveled in a front area of the end portion in such a way that they form surfaces of the end portion which extend obliquely with respect to the two planes of symmetry which are perpendicular to the surfaces of the needle region, so that they form a cutting edge containing the point of intersection of the two planes of symmetry. The result of this is that the lines of intersection of these facet surfaces form, with the two other mutually opposite lateral surfaces on one side, a more acute angle than they do on the other opposite side of the end portion. Another result is that, on the cutting edge, a pointed tip slightly offset with respect to the longitudinal axis of the needle is formed between the two facet surfaces and one of the side surfaces of the end portion.

The embodiment with the facet-like surfaces provides a robust tip which resists bending upon insertion into the surface of a tissue, and has a shape which can be easily worked. Moreover, measurements have shown that both the initial penetration force and the complete penetration force can simultaneously be lowered compared to the prior art.

In a needle with a quadrilateral needle cross section, for example, and with the needle tip configured according to the invention, depressions can extend along the outer surface of the needle region, or a slit can be formed through this needle region, such that a dialysis membrane can be provided in the depressions or in the slit. A microdialysis probe configured in this way is described for example in the patent application entitled "Microdialysis probe and method for the production thereof" which is from the same Applicant as the present application and bears the same application date. The microdialysis probe needle described therein is further improved by a needle tip according to the present invention, since introduction of the needle into a tissue is made less painful for a user.

In the present invention, the surfaces of the end portion may be worked by wet or dry grinding, or by honing or lapping. The edges along the lines of intersection between the surfaces of the end portion are advantageously deburred, and the arrangement of the surfaces of the end portion according to the present invention, as is described in, for example, the preceding illustrative embodiment, ensures a simple and rapid working of this area.

DETAILED DESCRIPTION

Figure 1A:
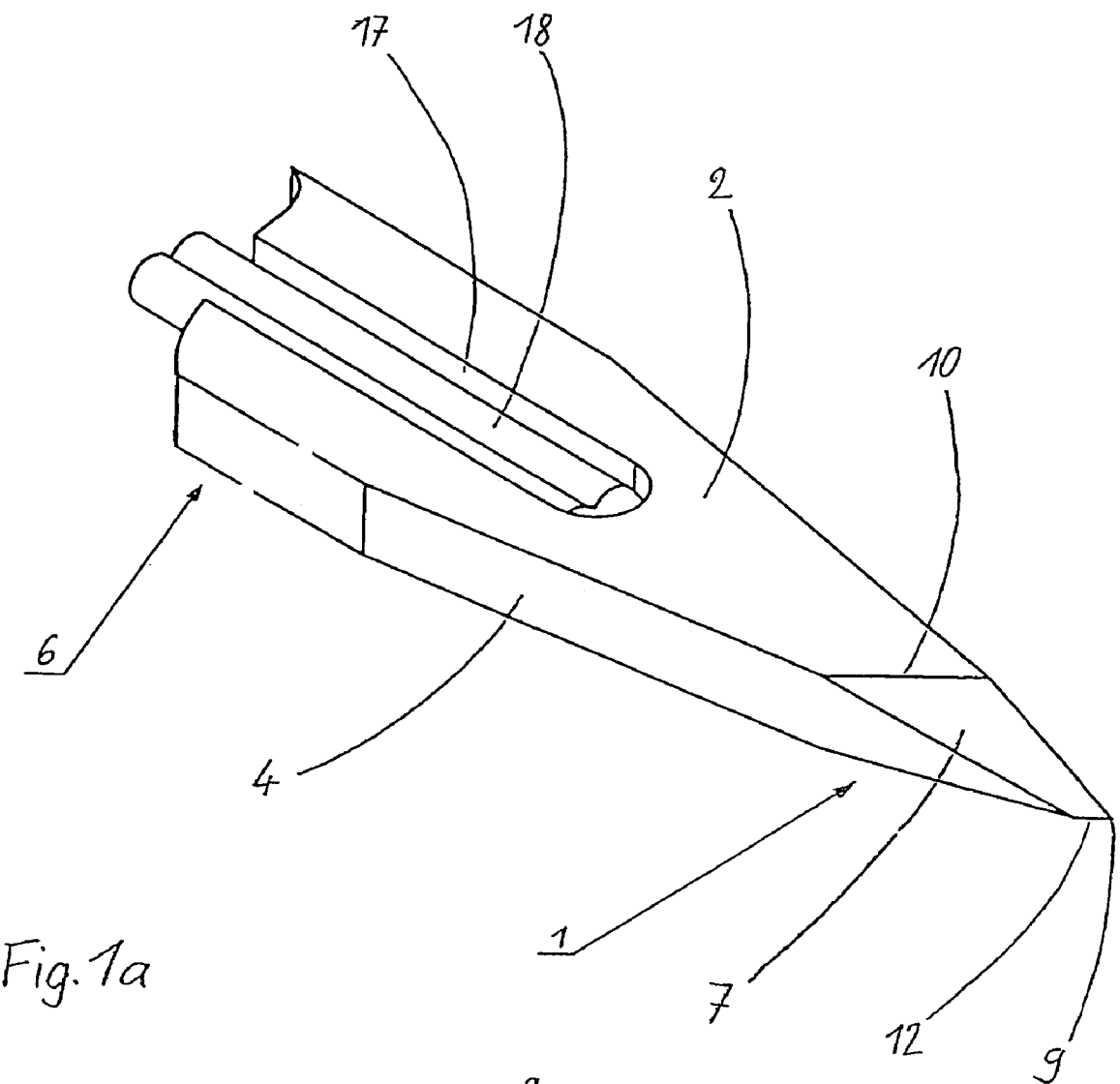
FIG. 1a is a perspective view of a preferred embodiment of a needle according to the present invention, with a faceted end portion.

FIG. 1a shows a needle for medical applications or uses, wherein the needle has an end portion 1 whose surfaces are faceted with respect to one another. The end portion 1, which may be referred to as the distal end portion, has a top 2, and a bottom 3 (not shown in FIG. 1a), which lie opposite one another and extend parallel with respect to one another. Perpendicular to the top 2 and the bottom 3, the end portion 1 has two side surfaces 4 and 5 (the latter not visible) which lie opposite one another and form, with the longitudinal axis of the needle, an angle A, which is shown in FIG. 1b. The two side surfaces 4 and 5 therefore extend parallel in one dimension. The needle region 6 of the embodiment in FIG. 1a has a rectangular cross section, where the surfaces of the broad side of the needle region 6 correspond to the surfaces of the top 2 and bottom 3 of the end portion 1, and where narrow surfaces of the needle region 6 which extend perpendicular to the broad surfaces merge into the side surfaces 4 and 5 of the end portion 1 via a beveling about the angle A. However, the needle region 6 could also have another suitable cross section, for example an oval cross section, in which case the top 2 and bottom 3 and the side surfaces 4, 5 of the end portion 1 could be generated by a correspondingly ground surface of such a needle. In some cases, the top and bottom would then not extend parallel to one another, and instead they would form an angle to one another.

In FIG. 1a, two facets or facet surfaces 7 and 8 (the latter not visible in FIG. 1a) are arranged at the end portion 1 and form a tip 9 and a cutting edge 12 of the needle. The facet surfaces 7 and 8 are oriented in such a way that, starting from the orientation of the top 2 or the bottom 3, they fall away in the direction of the needle tip 9 and, at the same time, fall away in the direction of the same side surface 4. The facet surfaces are therefore not oriented parallel to one another in any dimension. The facet surface 7 forms a line of intersection 10 with the top 2, and the facet surface 8 correspondingly forms a line of intersection 11 with the bottom 3, although the latter is not visible in FIG. 1a. Because of the orientation of the facet surfaces 7 and 8, the lines of intersection 10 and 11 and the cutting edge 12 are oriented obliquely with respect to the longitudinal direction or extent of the needle. The facet surfaces 7 and 8 are also oriented obliquely with respect to the planes of symmetry which are perpendicular to one another and intersect the surfaces of the needle region perpendicularly through the longitudinal axis of the needle.

Figure 1D:
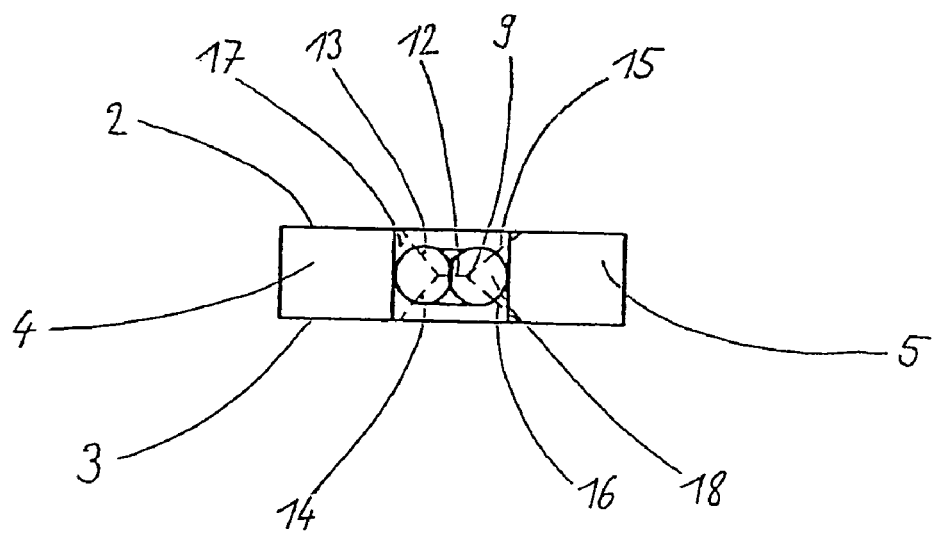
FIGS. 1b and 1c are longitudinal sectional views through the embodiment of the invention of FIG. 1a, FIG. 1d is a cross section through a needle region of the embodiment of the invention of FIG. 1a, FIG. 2 is a perspective view of another embodiment of a needle according to the present invention with an end portion with cone-shaped surfaces.
Figure 1B:
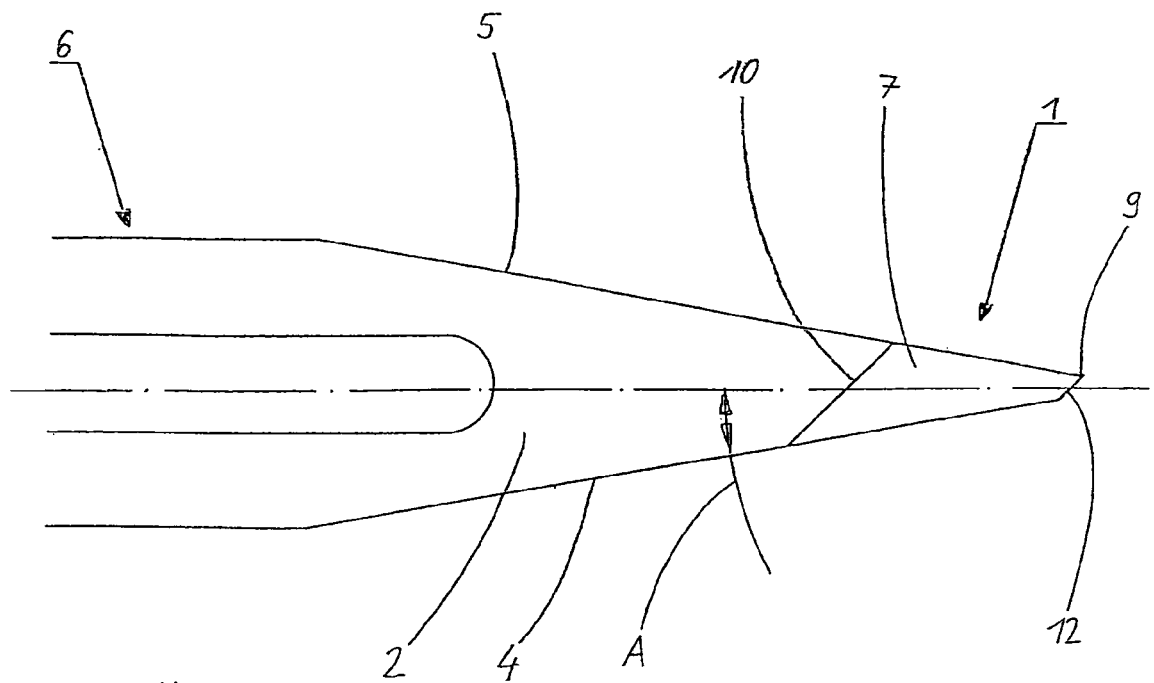
Figure 1C:
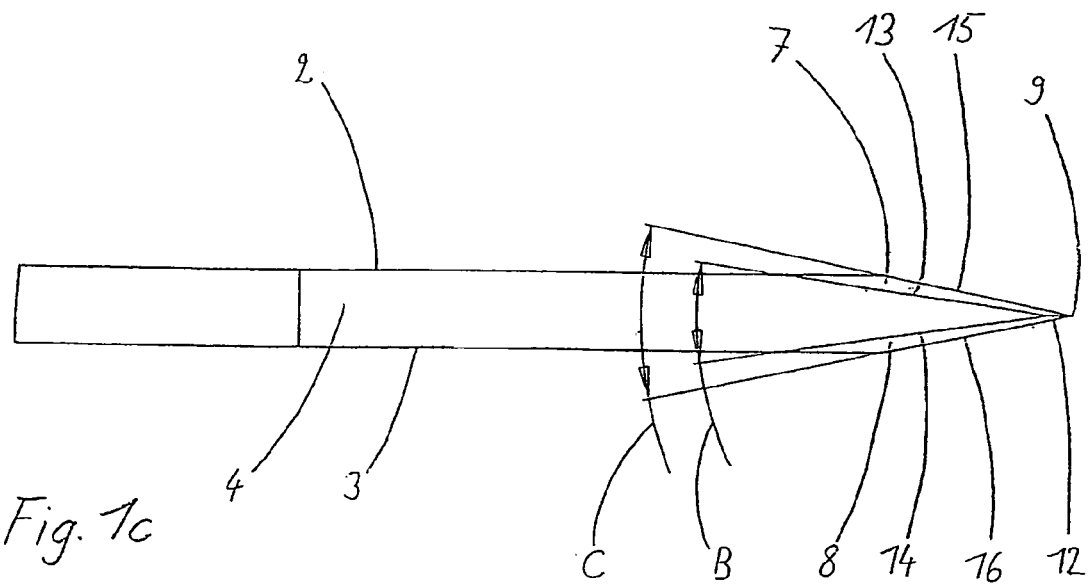

FIG. 1b shows a view of the top 2, and FIG. 1c shows a side view of the side 4, of the needle shown in FIG. 1a. In FIG. 1b, the side surfaces 4 and 5, in relation to the mutually parallel side surfaces of the needle region 6, are beveled by an angle A of 10° relative to the longitudinal axis of the needle, so that an angle of 20° results between the side surfaces 4 and 5. The angle A can, in principle, also be of another magnitude, but in preferred embodiments it may be between 5° and 30°. The cutting edge 12 preferably forms an angle of between 30° and 55° with the longitudinal axis of the needle. The beveled lines of intersection between the side surfaces of the needle region 6 and the side surfaces 4 and 5 of the end portion 1 are arranged symmetrically with respect to the longitudinal axis of the needle.

FIG. 1c shows the mutually parallel top 2 and bottom 3 and the likewise mutually opposite facet surfaces 7 and 8. The facet surface 7 is beveled relative to the top 2 in the direction of the longitudinal axis of the needle. At the same time, the facet surface 7 is also beveled in the direction of the side surface 4. In the same way, the facet surface 8 is beveled relative to the bottom 3 in the direction of the longitudinal axis and at the same time in the direction of the side surface 4. The result of this is that the lines of intersection of the facet surfaces 7 and 8 form different angles with the side surfaces 4 and 5. The line of intersection 13 between the facet surface 7 and the side surface 4 and the line of intersection 14 between the facet surface 8 and the side surface 4 form an angle B of about 16.5° in relation to one another. The angle B can also lie in the range around this value, preferably between 10° and 22°. By contrast, the line of intersection 15 between the facet surface 7 and the side surface 5, lying opposite the side surface 4, and the line of intersection 16 between the facet surface 8 and the side surface 5 form an angle C of 23.5°, which can also lie in a range around this value, preferably between 15° and 35°. The facet surfaces 7 and 8 are arranged symmetrically with respect to a plane of symmetry extending along the longitudinal axis of the needle and in the direction of the top and bottom 2, 3. The extent of the bevels of the facet surfaces 7 and 8 relative to the top 2 and bottom 3, respectively, is chosen such that the facet surfaces intersect in the cutting edge 12 and form a tip 9. The cutting edge 12 and the tip 9 lie on the plane of symmetry in the direction of the top 2 and bottom 3, and the point of intersection of the mutually perpendicular planes of symmetry of the needle region 6, i.e., also the longitudinal axis of the needle, lies on the cutting edge 12, but not in, on or at the tip 9. Therefore, the tip 9 is not arranged in a center point of symmetry of the needle.

The angle A between the side surfaces 4 and 5, the angles B and C between the facet surfaces 7 and 8 and the distance between the top 2 and bottom 3 are therefore adapted to one another in such a way that, in the end portion 1, the facet surfaces 8 and 9 intersect, and not the side surfaces 4 and 5. However, it would also be conceivable to choose the angles A, B and C and the distance between the mutually parallel faces 2 and 3 in such a way that the side surfaces 4 and 5 intersect in the front area of the tip of the end portion 1, which would result, however, not in the formation of a cutting edge 12 extending obliquely with respect to the longitudinal axis of the needle, but instead in the formation of an edge extending perpendicular to said longitudinal axis. FIG. 1b shows that the line of intersection 10 and the cutting edge 12 extend obliquely with respect to the longitudinal direction of the needle and thus also obliquely with respect to a direction perpendicular to the longitudinal direction of the needle.

FIG. 1d is a sectional view through the needle region 6 of the needle. The lines of intersection 13, 14, 15 and 16 between the facet surfaces 7 and 8 and the side surfaces 4 and 5 are indicated by broken lines. The cutting edge 12 is also indicated by a broken line. It will be seen that the cutting edge 12 lies on the plane of symmetry extending parallel to the top 2, but the tip 9 lies outside a second plane of symmetry extending perpendicular to said plane of symmetry. It will also be seen that the path from the lateral start of the side surface 4 to the start of the facet surfaces, i.e., to the line of intersection 12 in FIG. 1a, and the path between the start of the side surface 5 and the start of the facet surfaces differs.

The embodiment shown in FIGS. 1a-d has a pointed tip 9, by means of which the initial force needed for penetration is decreased. At the same time, this embodiment has a cutting edge 12 by means of which the overall force needed for penetration when inserting the microdialysis needle is likewise reduced. The surfaces of the end portion 1 may be manufactured, shaped or produced by suitable methods, including by wet or dry grinding using, for example, a surface-grinding device with a diamond cutter of grinding degree D500. The lines of intersection and points of intersection were deburred after the grinding, by which means it was possible to further decrease the force needed for penetration.

In the embodiment according to FIGS. 1a and d, the needle is used as the microdialysis needle of a microdialysis probe. For this purpose, the needle region 6 has a slit-like recess 17 which extends partially into the end portion 1. A dialysis membrane in the form of a hollow fiber 18 is arranged in the slit 17. The hollow fiber 18 is fitted in the slit 17 in such a way that it forms a supply line and a discharge line for a perfusion solution. For this purpose, two stretches or lengths of hollow fiber are arranged alongside one another and execute a reverse turn in the rounded end area of the slit 17 in or near the end portion 1. After the microdialysis needle has been introduced into a tissue, an exchange is able to take place between the hollow fiber membrane 18 and the tissue environment along the stretches of hollow fiber membrane and the reverse turn area, by means of which exchange the concentration, for example, of dissolved substances or the viscosity of the tissue fluid can be measured. FIG. 1d shows how the cross sections of the two stretches of hollow fiber membrane 18 are arranged in parallel alongside one another inside the slit 17. By means of a suitable method for bending the hollow fiber membrane, the latter can easily be applied inside the slit. Such a method is also described in the aforementioned application "Microdialysis probe and method for the production thereof" owned by the owner of the present invention.

Figure 2:
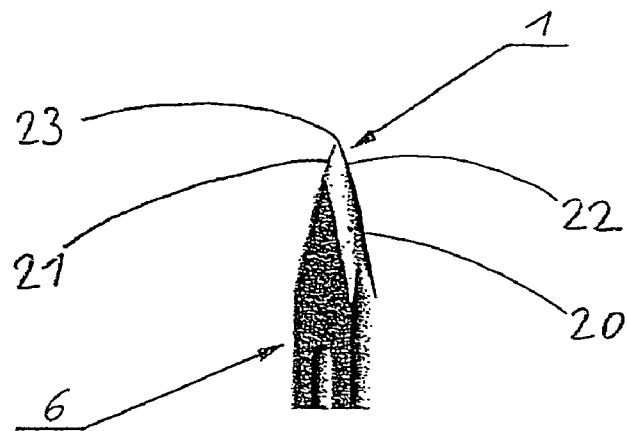

FIG. 2 shows a further embodiment of the present invention in which a end 1 of a needle is shown with a needle region 6 generally corresponding to FIG. 1. The end portion 1 in FIG. 2 has two cone-shaped surfaces 20 arranged on opposite sides and running or extending toward one another. The two cone surfaces 20 extend obliquely in the direction to the longitudinal axis of the needle and intersect at a center point of the cross section of the needle region 6. This produces two cutting edges 21 and 22 which lie opposite one another and taper to a point and form the needle tip 23. The needle tip 23 lies on the center point of the cross section of the needle, and the cutting edges 21 and 22 lie on a plane of symmetry which lies on the longitudinal axis of the needle and extends parallel to the narrow side of the rectangular cross section of the needle region 6. By means of the cone-shaped profile of a surface 20, the latter is more strongly curved in an area near the needle tip 23 than it is in an area near the needle region 6. By this means, a gentle transition from the cone-shaped surfaces 20 to the side surfaces of the needle region 6 can be produced.

Figure 3A:
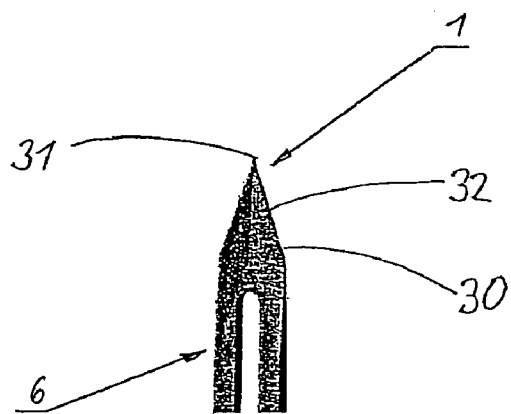
FIG. 3a is a perspective view of another embodiment of the present invention with a pyramid-like end portion.

FIG. 3a shows a further embodiment of the invention in which the end portion 1 has a pyramid-like shape. The needle region 6 of the needle is of rectangular shape as in FIGS. 1a-d. The end portion 1 of the needle has four diamond-like pyramid surfaces 30 which form a pyramid tip as needle tip 31 at the center point of the cross section of the needle region 6. The pyramid surfaces 30 are arranged symmetrically with respect to the planes of symmetry of the rectangular cross section of the needle region 6. A wide side of the cross section merges into two pyramid surfaces which together form an obtuse angle. The narrow side of the cross section merges into two pyramid surfaces which together form an acute angle, so that their line of intersection forms a cutting edge 32. Accordingly, a pyramid surface forms an obtuse angle with a pyramid surface adjoining it on one side, and it forms an acute angle with the pyramid surface adjoining it on the other side. The lines of intersection extend on the axes of symmetry of the cross section of the needle region 6.

Figure 3B:
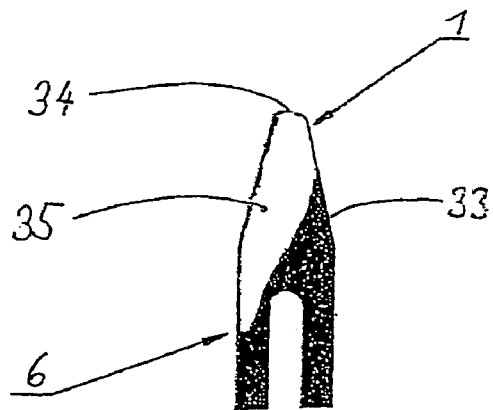
FIG. 3b depicts an embodiment of the present invention with a end portion in half pyramid form.

FIG. 3b shows another embodiment of a pyramid-like end portion 1 which forms a kind of half pyramid. The needle region 6 is rectangular, as in FIGS. 1a-d. In the end portion 1, the narrow sides of this rectangle are beveled in the direction of the longitudinal axis of the needle, so that they form side surfaces 33 which are symmetrical with respect to a plane of symmetry of the needle region. The wide surfaces of the needle region 6 are beveled in such a way that they are oriented obliquely with respect to both planes of symmetry of the needle region 6 and at the same time extend parallel to one another in one dimension. This produces two surfaces 35 which lie opposite one another and form a cutting edge 34. Because of the parallel arrangement of the surfaces 35, however, there is no needle tip, such as is present for example in the embodiment in FIGS. 1a-d. The cutting edge extends obliquely with respect to the lines of symmetry of the cross section of the needle region 1, but perpendicular to the longitudinal axis of the needle.

When producing the needles with a end portion according to the invention, it was found that, if the material is too soft, burrs unavoidably form on the edges and are difficult to remove without damaging the edges. A soft material, however, avoids the development of undesirably fine edges, for example on account of an imprecise processing operation.

For this reason, a material of moderate hardness is preferably used. A double-edged cut avoids the development of burrs. It was further found that the provision of polygonal cross sections both in the end portion and also in the needle region makes deburring easier without causing further damage.

In the embodiment according to FIGS. 1a-d, a value of 0.75 N was measured for the initial penetration force needed for passing through the surface of a tissue with a needle according to the invention, and a value of 0.9 N was measured for the complete penetration force needed for insertion of the needle into the tissue. In the case of an end portion configured in this way, the needle tip and the cutting edge of the needle are strong enough to ensure that, when the needle penetrates into a tissue, they are not subject to any bending or to any other change. The penetration forces in a needle according to the prior art, for example the needle from Therumo Medical Corporation, which has a smaller cross-sectional surface area in the needle region than do the needles according to the embodiments of the present invention, have values of 0.5 N to 0.7 N for the initial penetration force and 0.7 N to 0.9 N for the complete penetration force. A suture needle, for example with a diameter of 0.6 mm, requires a full penetration force of 2.5 N and a widely differing initial penetration force. Therefore, a needle according to the present invention, while having approximately the same cross section as a suture needle, and an even larger cross section compared to the needle from Therumo Medical Corporation, requires a lower penetration force or equally high penetration force, respectively.

The embodiments of the present invention have been described, and shown in the drawing, using the example of a microdialysis needle for a microdialysis probe. In principle, however, the needle according to the invention can also be used in other medical or biological fields, and for other purposes.

Embodiments of the present invention, including preferred embodiments, have been presented for the purpose of illustration and description. They are not intended to be exhaustive or to limit the invention to the precise forms or steps disclosed. The embodiments were chosen and described to provide the best illustration of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle for medical uses comprising a needle region and an end portion, the end portion comprising at least two discrete areas which intersect a longitudinal axis of the needle and each other whereby one of at least one line or point of intersection is formed between the at least two areas, whereby a distal end of the end portion is defined by the at least one line or point of intersection, the at least one line or point of intersection being within the distal projection of the perimeter of the needle region, whereby the two areas extend obliquely with respect to a first plane symmetry through the needle region that is parallel to a top surface of the needle region and a second plane of symmetry through the needle region that is perpendicular to the first plane of symmetry, whereby the at least one line or point of intersection forms a cutting edge and a needle tip, and whereby the cutting edge contains a line of intersection of the first and second planes of symmetry.

2. The needle as claimed in claim 1, wherein at least two discrete areas of the end portion extend toward one another in the distal direction.

3. The needle as claimed in claim 1, wherein the at least two discrete areas intersect a first side surface of the end portion in such a way that lines of intersection thus produced form a first angle, and intersect a second side surface of the end portion in such a way that the lines of intersection thus produced form a second angle, the first angle being greater than the second angle.

4. The needle as claimed in claim 1, wherein the at least two discrete areas intersect a first side surface of the end portion in such a way that lines of intersection thus produced form a first angle, and intersect a second side surface of the end portion in such a way that the lines of intersection thus produced form a second angle, the first angle being greater than the second angle, and the two side surfaces forming an angle with the longitudinal axis of the needle.

5. A needle for medical applications, comprising an elongate needle region and an end portion adjoining the needle region and forming a needle tip for insertion into tissue, wherein: a) the end portion is made of solid material, and b) the end portion has at least two discrete facet surfaces which intersect a longitudinal axis of the needle and each other such that a line of intersection is formed between the at least two facet surfaces, wherein the line of intersection defines a distal-most end of the needle, and forms the needle tip and a cutting edge which extends obliquely with respect to the longitudinal axis of the needle.

6. The needle as claimed in claim 5, wherein the line of intersection lies within the distal projection of the perimeter of a cross section of the needle region.

7. The needle as claimed in claim 5, wherein the line of intersection lies on at least one of a plane of symmetry and a center line of symmetry of a cross section of the needle region.

8. The needle as claimed in claim 5, wherein the at least two discrete facet surfaces are either planar, curved, or partially planar and partially curved.

9. The needle as claimed in claim 5, wherein at least two discrete facet surfaces of the end portion are arranged with mirror symmetry in relation to a plane of symmetry extending along the longitudinal axis of the needle.

10. The needle as claimed in claim 5, wherein the needle region has a polygonal cross section.

11. The needle as claimed in claim 5, wherein the at least two discrete facet surfaces of the end portion extend toward one another.

12. The needle as claimed in claim 11, wherein the at least two discrete facet surfaces extend obliquely with respect to two planes of symmetry through the needle region which are perpendicular to one another, and form the sharp cutting edge which contains the point of intersection of the planes of symmetry.

13. The needle as claimed in claim 11, wherein the at least two discrete facet surfaces intersect a first side surface of the end portion in such a way that lines of intersection thus produced form a first angle, and they intersect with a second side surface, generally opposite the first side surface, of the end portion in such a way that the lines of intersection thus produced form a second angle, the second angle being greater than the first angle, and the two side surfaces forming an angle with the longitudinal axis of the needle.

14. The needle as claimed in claim 13, wherein the angle ranges from about 5° to about 30°.

15. The needle as claimed in claim 13, wherein the angle ranges from about 10° to about 22°.

16. The needle as claimed in claim 13, wherein the angle ranges from about 15° to about 35°.

17. The needle as claimed in claim 5, wherein the edge is deburred.

18. A needle for medical applications, comprising an elongate needle region and an end portion adjoining the needle region and forming a needle tip for insertion into tissue, wherein:
- a) the end portion is made of solid material, and
- b) the end portion defines a top surface, a bottom surface, a first side surface, and a second side surface, wherein the top and bottom surfaces lie opposite each other and extend parallel with respect to one another, and the first and second side surfaces lie opposite one another and form a first angle with respect to a longitudinal axis of the needle;
- c) the end portion includes a first facet surface and a second facet surface which intersect the longitudinal axis of the needle and each other such that a first line of intersection is formed between the facet surfaces, the first and second facet surfaces are planar, and the first line of intersection defines a distal-most end of the needle, and forms the needle tip and a cutting edge which extends obliquely with respect to the longitudinal axis of the needle; and
- d) the first facet surface forms a second line of intersection with the top surface and the second facet surface forms a third line of intersection with the bottom surface, and wherein the second and third lines of intersection extend obliquely with respect to the longitudinal axis of the needle.

19. The needle of claim 18, wherein the first facet surface is beveled relative to the top surface towards the first line of intersection and towards the first side surface, and the second facet surface is beveled relative to the bottom surface towards the first line of intersection and towards the first side surface.

* * * * *